United States Patent [19]

Lazarus

[11] Patent Number: 4,781,583
[45] Date of Patent: Nov. 1, 1988

[54] ADJUSTABLE PLASTIC FILM MATRIX

[76] Inventor: Harry J. Lazarus, 36 Knox La., Englishtown, N.J. 07726

[21] Appl. No.: 46,527

[22] Filed: May 4, 1987

[51] Int. Cl.$^4$ .................................................. A61C 5/04
[52] U.S. Cl. .................................................... 433/39
[58] Field of Search ............................ 433/39, 60, 147

[56] References Cited

U.S. PATENT DOCUMENTS 3,921,299  11/1975  Lazarus .................... 433/39
4,523,909  6/1985   Lazarus .................... 433/39

Primary Examiner—Robert Peshock
Attorney, Agent, or Firm—McGlew and Tuttle

[57] ABSTRACT

A dental matrix band for engaging around a tooth comprises a plastic sheet member which includes a straight winding portion which can be wound into a coil and a curved tooth engaging portion which is wrapped around to form a tooth engaging band. A lock loop having inner and outer legs is engaged onto overlapping portions of the band to hold the band in position. The locking loop has interior notches which form a gingival inwardly directed bend and tooth contacting point and an elongated gingival open area to provide band's diametric adjustability prior to seating matrix on a tooth, as well as a crimp structure for crimping the occlusal edge of the band to form an occlusal concavity. The coil may be conical and polygonal in shape to more accurately receive a winding burr of a winding tool. The coil is rotatable to tighten the band around a tooth. A retaining end of the sheet material which is on the inside of the band is provided with an elongated laminate to reinforce the plastic band underlying the rotatable coil which is adjacent said retaining end. The coil is wound against this supporting, reinforced area which prevents underlying band from collapsing and being "wrapped-under" by coil which pulls the matrix material through the lock loop with winding of the coil.

26 Claims, 4 Drawing Sheets

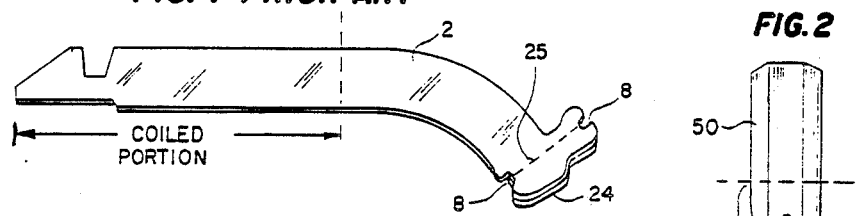
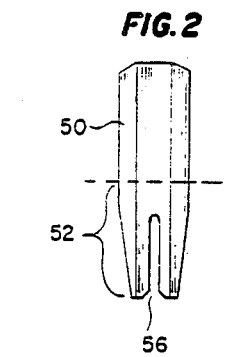
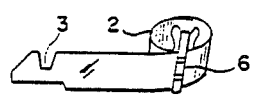
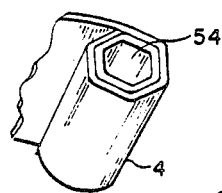
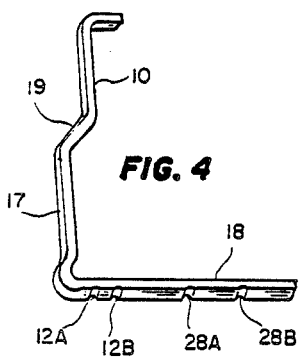
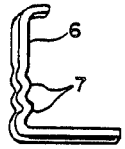
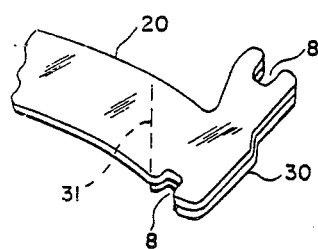
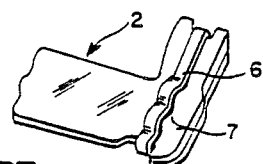

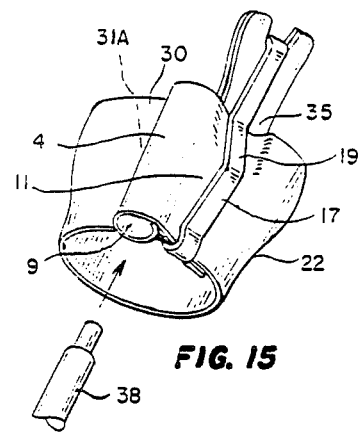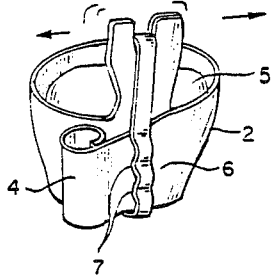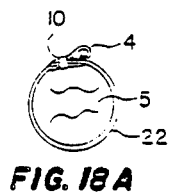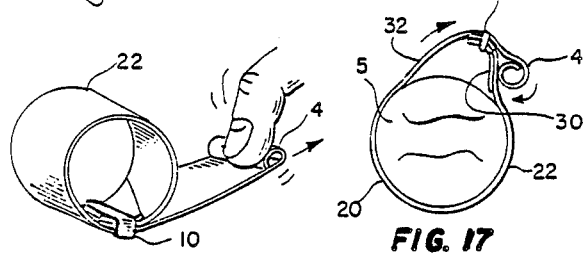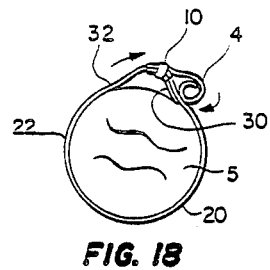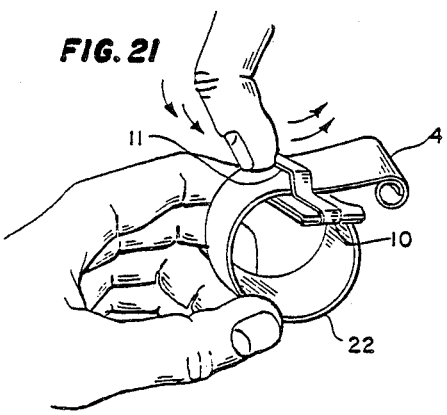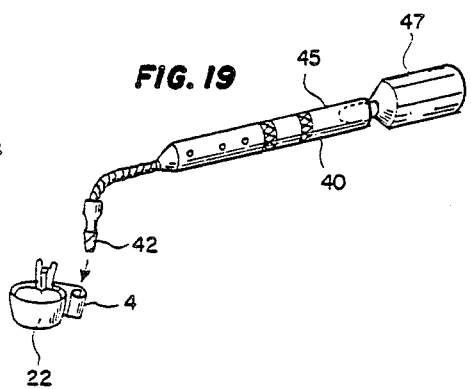

ADJUSTABLE PLASTIC FILM MATRIX

FIELD AND BACKGROUND OF THE INVENTION

The present invention relates in general to dental matrices for engaging around a tooth, and in particular to a new and useful dental matrix made primarily of plastic material, requiring no external retainer for retaining the matrix on a tooth, and being adjustable for both increasing and decreasing the initial diameter of the matrix so that it can be used with teeth having different diameters.

A retainerless steel dental matrix was introduced by the present inventor in his U.S. Pat. No. 3,921,299 entitled RETAINERLESS DENTAL MATRIX AND METHOD OF MANUFACTURE, issued Nov. 25, 1975 and hereinafter referred to as the -299 patent. The -299 patent discloses the use of a lock loop for engaging around the steel matrix which includes undulations or ripples referred to as "impregnators" in the patent. FIG. 7 of the present application shows a lock loop 6 before it has been engaged onto a matrix and carrying the impregnators 7.

Prior to tightening the steel matrix on the tooth, the lock loop fits loosely over the matrix. The metal matrix is adjustable prior to being seated on the tooth. Tightening of the matrix is achieved by winding a coil which is provided on the matrix using a winding tool such as that disclosed by the inventor's U.S. Pat. No. 3,852,884 entitled WINDING AND TIGHTENING TOOL AND METHOD OF MANUFACTURING SAME, issued Dec. 10, 1974 and hereinafter referred to as the -884 patent.

Winding of the coil which in turn causes tightening of the band also causes metal of the band adjacent to the coil to rise up and be impaled on the sharp edges of the impregnators on the inside of the lock loop. This causes a locking of the matrix in its tightened position. The impregnators actually work harden the metal of the matrix which securely locks the matrix in position.

The present inventor has also introduced a plastic matrix which is disclosed in his U.S. Pat. No. 4,523,909 entitled PLASTIC DENTAL MATRIX AND METHOD OF MANUFACTURING SAME, issued June 18, 1985 and hereinafter referred to as the -909 patent. To accomodate the lower winding torques which are appropriate for plastic bands, the inventor also disclosed a dual winding tool in his U.S. Pat. No. 4,551,097 entitled DUAL-TORQUE WINDING AND TIGHTENING TOOL, issued Nov. 5, 1985, hereinafter referred to as the -097 patent.

The lock loop of the plastic matrix in the -909 patent included impregnators 7 as shown in FIG. 7. It has been found however that this provides an insufficient locking effect for the plastic matrix. While increasing the sharpness of the impregnators did increase the locking capacity somewhat, it also tended to tear the plastic matrix. Sharpened impregnators were thus found inappropriate for the plastic matrices. Notably impregnators do not work harden the plastic matrix of the -909 patent as they did the metal matrices.

An attempt was made to more securely clamp the lock loop onto the plastic matrix. While this did improve the ability of the lock loop to lock the matrix in position, it deprived the dentist of his ability to adjust the diameter of the matrix prior to seating it on the tooth. Without being able to adjust the starting diameter of the matrix, a larger supply of differently sized matrices would be necessary to accomodate the different sized teeth. The number of different sizes necessary would become impractically large. By making the plastic matrix adjustable in its initial diameter, far fewer different matrix sizes need be stocked.

It is important to note that even if an attempt is made to seat a matrix having only a slightly smaller diameter than a tooth, the matrix tends to collapse as the dentist tries to force the matrix down around the larger diameter tooth. The difference in diameter between the matrix and the tooth may even be so small as not to be apparent to the dentist until he actually tries to fit the matrix on the tooth. By making the matrix adjustable the dentist can provide a safety margin in making sure the matrix is at least bigger than the tooth before an attempt is made to fit the matrix on the tooth.

FIGS. 10 and 11 illustrate problems which may occur when utilizing the plastic matrix of the -909 patent.

As shown in FIG. 11, if the lock loop 6 is very firmly clamped onto the matrix for producing a secure locking of the matrix, and if the matrix is used on a tooth having too small a diameter for the matrix size, when a dentist attempts to roll the coil 4 using the winding tool, rather than pulling the excess portion 33 of the matrix 2 through the lock loop 6 as is required to adapt the matrix to the tooth, the coil tends to destructively "wrap under" at 36 the lock loop, without pulling the excess through the lock loop. The matrix thus fails to be tightened around the tooth.

FIG. 10 illustrates a technique which is sometimes used by a dentist to insure the correct tightening of a matrix 2 around an undersized tooth 5. The dentist utilizes his finger intra-orally to hold the matrix at the lock loop 6 while the coil 4 is wound. This then permits excess matrix portion 33 to be wound up on the coil and tightened on the tooth. This intra-oral manipulation is an awkward nuisance in the cluttered intra-oral area, and makes the use of the matrix more difficult.

FIG. 1 shows a plastic blank sheet member which is used to form the matrix 2 and which includes a substantially straight coiled portion with an end having a crosshair or notch 3 for receiving a tool for forming the coil. The matrix also includes an intermediate curved tooth engaging portion that terminates at the receiving means in the form of an enlarged end that includes an extra laminated layer 24 with an edge 25 and a pair of opposed notches 8. This retaining means serves to receive and engage the lock loop of FIG. 7. FIG. 8 shows the lock loop 6 in place on the end of the matrix 2.

FIG. 16 illustrates another problem of the plastic matrix in patent -909. Since the impregnators 7 are near the middle of the matrix and the engagement of the lock loop 6 is rather tenuous at the top and bottom of the matrix, the matrix tends to wobble or pivot in the direction of the double arrows when the dentist inadvertently bumps against the outer most part of the lock loop, causing the lock loop to pivot. This pivoting has been found to cause the loosening of the coil and the matrix 2 from around the tooth 5.

SUMMARY OF THE INVENTION

The present invention is drawn to a plastic matrix and its method of manufacture which overcomes the problems of the plastic matrix in the -909 patent.

According to the present invention, the lock loop is configured to permit the increasing or decreasing of the initial diameter for the matrix. Despite this adjustability, the lock loop securely locks the matrix in place on the tooth.

Another feature of the invention is the provision of a conical polygonal coil which is preformed on the matrix and which is more positively engaged and wound by the winding tool.

The retaining area of the matrix which receives the lock loop is also provided with a somewhat elongated angular laminate which is positioned under the coil. This prevents a "wrap under" of the matrix such as that shown in FIG. 11. This angulation eliminates the need for the dentist's cumbersome finger pressure on the lock loop as shown in FIG. 10 even if the matrix is somewhat oversized. On the tooth, the stiff, angulated laminate resists inward pressure of the winding coil to prevent "wrap-under". The point on the angle directs the coil over, rather than under the laminate edge.

According to another feature of the invention, the occlusal edge of the matrix band is provided with an occlusal concavity which is concave inwardly toward the interior of the matrix under the lock loop. The lock loop is shaped with a contra-angle to create and retain this concavity. The lock loop also includes a gingival tooth contact point which engages a tooth wrapped by the matrix band. The concavity frictionally grips and pockets the lock loop against pivoting laterally which would unroll the coil and loosen the matrix's tight lock on the tooth. In this way, when the coil is tightened, the lock loop frictionally engages the tooth at its gingival edge and simultaneously the occlusal end of the lock loop is pocketed in said concavity, against pivoting at said occlusal edge. This pocketing, combined with the gingival tooth contact effectively avoids pivoting of the lock loop as shown in FIG. 16, which would otherwise result in loosening of the matrix. Notably, the plastic is soft, prior to the seating of the matrix, which permits said relatively soft plastic to be drawn through the lock loop for diametric adjustability of the matrix. Conversely, when the matrix is tightened onto a tooth, the occlusal band edges and the concavity itself stiffens and is much less soft than previous to being seated. This firmer, stiffer plastic of the tightened band, pockets the lock loop in the crimp of the lock loop legs and in said concavity area, which prevents said lateral pivoting of the lock loop, and thus retains the matrix's tight fit on the tooth. Thus, the improved loop, in combination with both the novel open area and the concavity, provides both the ability to adjust the plastic matrix, well as keep it tight on the tooth.

The invention also includes a method of forming the conical polygonal coil by using a conical polygonal winding mandrel which is preferably hexagonal and which has a slot for receiving the cross hair or notch at one end of the matrix sheet material. A heated coil searing rod is then inserted into the gingival end of the coil to fuse the end, and fix its shape, for ready engagement of coil winder.

Accordingly an object of the present invention is to provide a dental matrix made from a plastic sheet of material and including a novel lock loop wherein the matrix and loop are configured to permit adjustability in the diameter of the plastic matrix band while insuring a secure locking of the matrix on the tooth.

A further object of the invention is to provide a method of making a plastic matrix readily adjustable, prior to seating same on a tooth.

A still further object of the invention is to provide a plastic dental matrix which is simple in design, rugged in construction and economical to manufacture.

There are more than one embodiments disclosed.

BRIEF DESCRIPTION OF THE DRAWINGS

In the drawings:

FIG. 1 is a plan view of a plastic blanked sheet material for making a matrix in accordance with the -909 patent;

FIG. 1A is a view of the sheet material of FIG. 1, rolled into a lock loop;

FIG. 2 is a partial side elevational view showing a conical-polygonal formed mandrel for winding the coil of the matrix in accordance with the present invention;

FIG. 2A is a fragmentary perspective view of the conical-polygonal winding coil of the present invention;

FIG. 3 is a fragmentary perspective view of the lock-loop-retaining end of a plastic blanked sheet member for making the matrix of the present invention and illustrating an elongated laminate;

FIG. 4 is a perspective view showing the lock loop of the present invention in an open position before it is engaged onto the plastic sheet member to form the matrix;

FIG. 5 is a perspective view, with portions cut away, of the inventive matrix with the lock loop of FIG. 4 in its assembled condition, on a tooth;

FIG. 6 is a fragmentary perspective view similar to FIG. 3 but showing the lock loop in position;

FIG. 7 is a view similar to FIG. 4 showing the lock loop of the -909 patent;

FIG. 15 is a perspective view showing the inventive matrix during its manufacture and just before the setting of the inner diameter of the winding coil;

FIG. 16 is a perspective view similar to FIG. 12 but showing the matrix of the -909 patent and illustrating how inadvertant bumping of the lock loop retaining end of the lock loop can cause lateral pivoting of the lock loop which unrolls the coil and loosens the matrix;

FIG. 17 is a top plan view of the inventive matrix on a tooth showing an initial stage of winding of the coil when the matrix is far larger than needed for the diameter of the tooth;

FIG. 18 is a view similar to FIG. 17 showing an intermediate position during the winding of the coil, and showing how the stiff angular laminate resists the coil's pressure to "wrap-under" without use of a finger on the lock loop;

FIG. 18A is a view similar to FIG. 18 showing the final tightened position for the matrix, without "wrap-under";

FIG. 19 is a perspective view showing the matrix of the present invention on a tooth and illustrating a winding tool which is in accordance with a co-pending application by the inventor entitled FINGERLESS DUAL-TORQUE LIMITING AND WINDING TOOL.

FIG. 20 is a perspective view illustrating how the coil of the present invention can be unwound as an initial step in increasing the diameter of the matrix band;

FIG. 21 is a perspective view illustrating how the open-area of the lock loop of the present invention can be wiggled and pushed to enlarge the diameter of the matrix-band;

DESCRIPTION OF PREFERRED EMBODIMENTS

Figure 9:
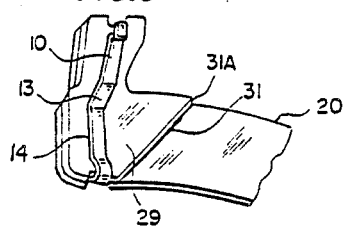
FIG. 9 is a fragmentary perspective view similar to FIG. 6 but showing the interior of the retaining end of the inventive matrix with the lock loop in place.
Figure 8:
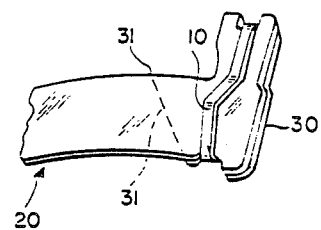
FIG. 8 is a view similar to FIG. 6 showing the lock-loop-retaining end and lock loop of the -909 patent.
Figure 10:
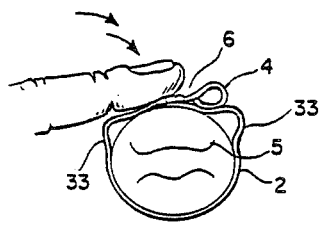
FIG. 10 is a planned view showing how a dentist's finger is used to hold the lock loop of the -909 patent to avoid a "wrap under" of the matrix material.

Referring to the drawings in particular, the present invention comprises a plastic blanked sheet member similar to that shown in FIG. 1 which includes a coiled or windable and substantially stright portion having a first tail end which carries a cross-hair or notch 3 that can be engaged by a mandrel for winding the coil of the present invention. The sheet material 2 has an intermediate curved tooth engaging portion which ends at a second end that carries lock loop receiving means in the form of notches 8. Unlike the -909 patent, however, rather than a short laminate 24 which extends only up to the notches or perhaps a little further, the present invention uses a larger elongated, angled laminate 30 which is illustrated in FIGS. 3, 6 and 9. This laminate may be made of a second layer of plastic material. The laminate is provided with angle 31, and pointed end 31-A. This angle 31 and point 31-A direct the winding coil over, rather than under the laminate, preventing "wrap-under".

As with the -909 patent it is particularly advantageous to utilize transparent plastic so that light curable tooth restorable material retained within the matrix wall and on the tooth can be cured by directing said light through the transparent matrix wall.

FIG. 2 illustrates a hexagonal winding mandrel 50 having a tapering conical area 52 and a slot 56 for receiving the cross hair 3 at the first end of the blanked sheet material. By using mandrel 50, the inside diameter or ID 54 of the coil 4 is formed to have a conical hexagonal, or more generally polygonal configuration, which is selected to match the polygonal configuration of a winding burr 42 of a winding tool 40 shown in FIG. 19. As more comprehensively explained in the co-pending application entitled FINGERLESS DUAL-TORQUE LIMITING AND WINDING TOOL, winding tool 40 has a handle portion 47 which is grasped in the palm and a winding portion 45 which is rotated by the fingers of the same hand to rotate the winding head burr 42 after it has been inserted into a coil 4.

Another step in the production of the coil 4 is illustrated in FIG. 15. According to this step of the manufacturing process, a heated probe or coil-searing rod having about the same outside diameter as the inside diameter of the coil, is inserted into the gingival opening 9 of the coil 4 to fuse the ends of the coil windings and to set and lock the inside diameter of the coil. This insures proper engagement of the burr in the coil when the coil is to be wound.

As shown in FIGS. 3, 6 and 9, the elongated laminate 30 includes an elongated portion 20 which extends over the interior surface of the improved matrix blank 20 up to an inclined edge 31 which is inclined toward the gingival end of the lock loop 10. The laminate is curved concavely outwardly as viewed in FIG. 9 which concave shape is further fixed by a curved inner leg 14 of the lock loop 10.

The provision of elongated laminate 30 combined with angle 31, and point 31-A permits winding of coil 4 without the dentist having to place a finger against the lock loop. The sequence of FIGS. 17, 18 and 18A can thus be achieved for a correct winding of the matrix on a tooth without "wrap-under". As shown in FIG. 17, the coil 4 bears against the part of the matrix which is supported by the firm elongated laminate 30. Winding of coil 4 in the direction of the small arrow thus draws the matrix material 32 through the lock loop 10 in the direction of the larger arrow to secure the band portion 22 of the matrix 20 on the tooth 5. FIG. 18 shows the band in further progress and FIG. 18A shows the band after it has been fully locked on the tooth.

In this way even an oversized matrix can be used without first having to adjust the diameter of the matrix, without using a finger, and without "wrap-under" occurring, as in FIG. 18-A.

To make the inventive matrix adjustable in its band diameter, the lock loop 10 is provided with a new configuration as best shown in FIGS. 4, 5 and 9.

To this end, the lock loop 10 includes an outer leg 17 which has a gingival open area which is bent inwardly with respect to the matrix. The lock loop 10 also includes an inner leg 18 which has a plurality of interior notches 12A, 12B, 28A and 28B, which are all on an inner surface of the leg 18 with respect to the matrix band. With the inner leg 18 engaged over the interior of the plastic sheet member as shown in FIG. 5, the notches 12A and 12B are adjacent the gingival end of the matrix bank and form an inwardly projecting gingival tooth contacting point 15. Notches 12A and 12B also define the precise bend area of the lock loop, to create the gingival open area 11 which extends up to notch 28-B. This open area provides internal lock loop clearance for adjusting the plastic material inside the lock loop prior to seating the matrix and winding the coil to lock the matrix onto a tooth, thus providing said diametric adjustability.

The notches 28A and 28B are positioned near the occlusal edge of the matrix band 22 as shown in 15 and interiorly of the crimp bend area 19. Together the bend area 19 and the inner leg 18 adjacent the notches 28A and 28B form an occlusal concavity and crimp structure 13 which depresses the plastic matrix material to form a matrix-locking occlusal stiffened concavity 34 which is visible in FIGS. 12 through 15. This stiffness occurs only when the matrix is wound tightly on a tooth. By the winding and forming of the tight band circlet, said stiffened concavity pockets the lock loop against pivoting. Yet, prior to tightening on the tooth, the matrix is slidably adjustable through the lock loop.

As shown in FIG. 9, the portion 14 of the inner leg 18 between the notches 12B and 28A is curved concavely when viewed from the interior of the matrix. This helps bend the retaining end along with the laminating 30 into a curved anatomically adapted surface for closely engaging a tooth.

Figure 22:
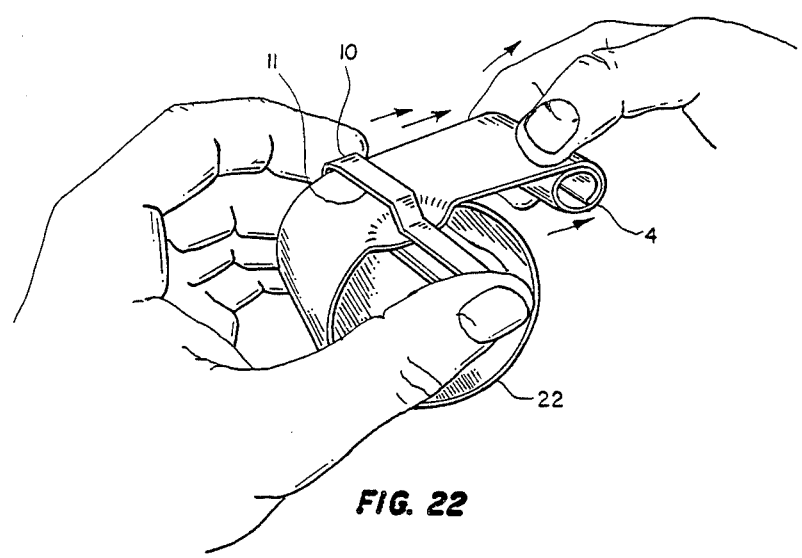
FIG. 22 is a perspective view illustrating how the diameter of the matrix band in accordance with the present invention can be reduced.

Before the inventive matrix is engaged onto a tooth, the diameter of its band 22 can be adjusted as illustrated in FIGS. 20, 21 and 22.

As shown in FIG. 20, in order to enlarge the diameter of the band 22, the coil 4 is first partly unwound in the direction of the arrow shown in FIG. 20. As shown in FIG. 21, the lock loop can then be wiggled and pushed to manipulate it out toward the coil 4. This permits part of the band 22 to slide along the lock loop 10. Prior to seating the matrix on a tooth the occlusal concavity 34 as shown in FIG. 15, the plastic material is sufficiently resilient to permit movement through the concavity and open area 11 of the lock loop 10.

FIG. 22 illustrates how the diameter of the band 22 can be reduced by firmly grasping the coil 4 in one hand and the lock loop 10 in the other hand and gently pulling the coil to the right to slide some of the band material under the lock loop 10.

The occlusal concavity formed by said crimped bends, in the lock loop's inner and outer legs, provides both slidable diametric adjustability to the soft matrix prior to seating same on a tooth. Thereafter upon tightening the matrix on a tooth, said occlusal edge and concavity stiffen, with said lock loop becoming pocketed into said stiffened concavity to prevent said pivoting and loosening of the matrix from its tight fit on the tooth.

The lock loop 10 of the present invention can be wiggled and teased to permit adjustment of the diameter of the matrix band. This is possible because of the open area 11 shown in FIG. 5 and is not possible in the excessively required tight lock loop of the -909 patent, which does not provide said open area 11.

Despite this pre-seating adjustability once the coil 4 is wound and the matrix is tightened on a tooth the concavity and crimp 13 of the lock loop 10 forms a pocketed, fixed and secure non pivoting, frictional connection with the concavity of the matrix, locking the matrix on the tooth.

Figure 14:
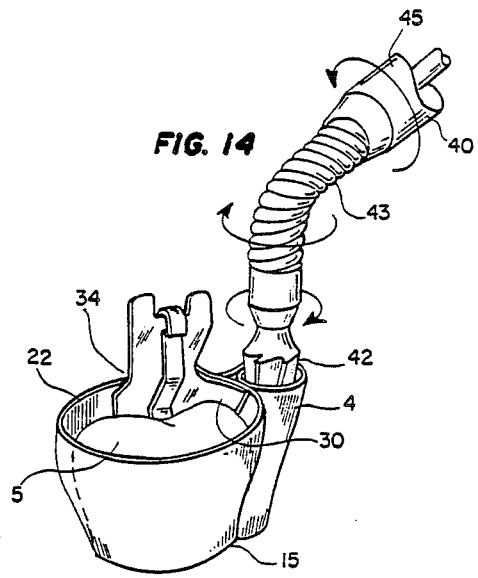
FIG. 14 is a perspective view showing the matrix band of the present invention on a tooth and used in conjunction with a coil winding tool.

Because of the gingival contacting point 15, when coil 4 is wound as shown for example in FIG. 14, the point 15 is pressed in frictional contact against the gingival area of a tooth 5 (FIG. 5) thus joining with crimp 13 to prevent pocketed lock loop from pivoting.

The lock loop firmly engages the matrix material broadly at the wide occlusal concavity at crimp 13, while the lock loop bears against the gingival edge of tooth, thereby rocking and pivoting of the lock loop is avoided so that the problem of having the matrix come loose as shown in FIG. 16 is avoided. Further, because crimp 13 is a broad crimp, unlike the sharp impregnators of the -909 patent, which encourage pivoting, said broad crimp of this invention prevents pivoting which loosens the matrix.

Figure 13:
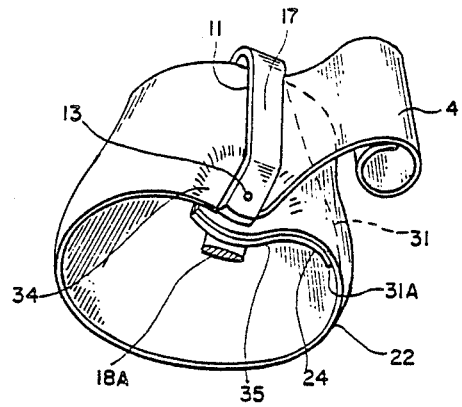
FIG. 13 is a perspective view of the matrix shown in FIG. 12 after the top of the lock loop has been cut off, and the matrix has been removed from the tooth and particularly illustrating the occlusal concavity on the occlusal edge of the matrix band.
Figure 11:
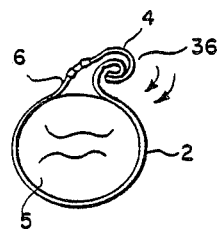
FIG. 11 is a view similar to FIG. 10 but showing how the matrix material is "wrapped under" when a dentist attempts to wind the coil of the -909 patent without holding the lock loop, or is unsuccessful in reaching the lock loop.

It is noted that the concavity 34 as shown in FIGS. 13 and 15 similar to a baseball catcher's mitt which is meant to catch and retain a baseball in a concave pocket while the present invention retains the lock loop in such a pocket, the prior matrix was provided with no such concave pocket.

After the matrix is wound on the tooth as shown in FIG. 14 by seating the burr 42 in the coil 4 and rotating the flexible sleeve 43 by rotating the rotatable tool handle 45 of the winding tool 40, the light-curable restorative material is cured using a beam light. Said light readily passes through the transparent plastic matrix film material to cure said restorative material in said tooth.

Figure 12:
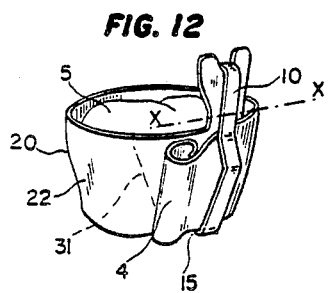
FIG. 12 is a perspective view showing the matrix of the present invention tightened and locked on a tooth.

After the curing operation the extended, finger-like portion of the matrix as well as the top of the lock loop 10 is severed along the line X—X as shown in FIG. 12. This leaves the severed, openable structure shown in FIG. 13 which thereby can easily be removed from the tooth. FIG. 13 is also instructive in illustrating the contours of the occlusal concavity 34 which is at the occlusal end of the inwardly concave laminate 20. Occlusal concavity 34 is at the occlusal band edge 35.

While specific embodiments of the invention have been shown and described in detail to illustrate the application of the principles of the invention, it will be understood that the invention may be embodied otherwise without departing from such principles.

What is claimed is:

1. A dental matrix band for engaging around a tooth, comprising: A plastic sheet member having a windable portion carrying a first end of said sheet member, a curved intermediate tooth engaging portion carrying a second end of said sheet member, said second end of said sheet member defining a receiving area, said tooth engaging portion being wrapped to form a matrix band with a part of said tooth engaging portion which is adjacent to said windable portion overlying said receiving area, said windable portion being wound to form a winding coil, and a lock loop engaged over said receiving area and said part of said tooth engaging portion, said lock loop permitting a sliding withdrawal of said tooth engaging portion with a winding of said winding coil by a dentist's matrix coil winding tool to tighten said band around a tooth by winding said coil against said lock loop which locks the matrix on the tooth, said lock loop having an outer leg engaged against an exterior of said part of said tooth engaging portion, said outer leg having an occlusal inwardly extending crimp bend area for bending an occlusal edge of said band inwardly, said lock loop having an inner leg engaged against an inner surface of said receiving area, said inner leg having a gingival tooth contacting point extending inwardly of said band and an occlusal crimp bend positioned adjacent to said crimp bend of said outer leg.

2. A dental matrix band according to claim 1 wherein said outer leg and said inner leg together define a non-crimped open area adjacent said gingival tooth contacting point with a substantial portion of said band being disposed in said open area, said open area permitting diametric adjustability of said matrix prior to seating it on a tooth.

3. A dental matrix band according to claim 2 including a plurality of notches on an interior surface of said inner leg with respect to said matric band, said notches defining said gingival tooth contacting point and said occlusal concave crimp bend of said inner leg.

4. A dental matrix band according to claim 3 wherein said inner lock-loop leg includes a curved inner leg portion which is curved concavely outwardly with respect to said matrix band and extending between said contacting point and said crimp bend of said inner leg.

5. A dental matrix band according to claim 1 wherein said matrix band includes an occlusal edge with an occlusal concavity between said crimp bends of said inner and outer legs.

6. A dental matrix band according to claim 4 wherein said matrix band includes an occlusal edge with an occlusal concavity between said crimp bends of said inner and outer legs.

7. A dental matrix band according to claim 1 wherein said inner leg has a gingival tooth contacting point extending inwardly of said band to frictionally press said contacting point against the gingival of a tooth to co-function with said extended crimp bend area to stabilize said lock loop against matrix-loosening pivotability.

8. A dental matrix band according to claim 5 wherein an occlusal portion of both legs are formed to provide overall broadly crimped, inner surface contact of said legs with said occlusally crimped matrix being sandwiched between said legs to pocket the occlusal portion of said lock loop in said occlusally crimped concavity against lock loop pivotability after tightening said matrix band.

9. A dental matrix band according to claim 6 wherein an occlusal portion of both legs are formed to provide an overall broadly crimped, inner surface contact of said legs with said occlusally crimped matrix sandwiched between said legs to pocket the occlusal portion of said lock loop in said occlusally crimped concavity against lock loop pivotability after tightening said matrix band.

10. A matrix band according to claim 1 including an elongated laminate laminated to said receiving area and extending partly onto said tooth engaging portion for underlying said coil for supportively reinforcing said band against wrap-under force resulting from winding of said coil.

11. A dental matrix according to claim 10 wherein said laminate has an inclined edge which is inclined at an angle toward said gingival tooth contacting point of said lock loop.

12. A matrix band according to claim 4 including an elongated laminate laminated to said receiving area and extending partly onto said tooth engaging portion for underlying said coil for reinforcing said band against wrap-under forces resulting from winding of said coil.

13. A dental matrix according to claim 1 wherein said coil is conical and polygonal and reduces in cross section from the occlusal edge to the gingival edge of the matrix band.

14. A matrix band according to claim 13 wherein said coil is heat treated to set its inside diameter.

15. A dental matrix according to claim 4 wherein said coil is conical and polygonal and reduces in cross section from the occlusal edge to a gingival edge of the matrix band.

16. A matrix band according to claim 1 wherein said plastic sheet member is made of transparent material.

17. A dental matrix according to claim 4 wherein said plastic sheet member is made of transparent material.

18. A lock loop for locking a retainerless plastic dental matrix comprising an outer leg for engaging a plastic matrix band having an occlusal edge and a gingival edge, said outer leg having a gingival end and an occlusal end, said outer leg having an inwardly extending crimp bend at said occlusal end, said lock loop having an inner leg which is bent to extend substantially along said outer leg, said inner and outer legs together forming an open area extending substantially from said gingival end to said occlusal crimp bend area, said inner leg being bent to form an inwardly extending gingival tooth contacting point at the gingival end and an inwardly extending occlusal concave crimp bend adjacent to, and substantially formed for mating with inner contours of said crimp bend of said outer leg.

19. A lock loop according to claim 18 including at least one notch at said gingival end for defining said contacting point and at least one notch at said occlusal end for defining said crimp bend of said inner leg.

20. A lock loop according to claim 19 including an outwardly concave portion of said inner leg extending between said notches.

21. A lock loop according to claim 18, wherein said mating is formed to sandwich said occlusal matrix edge into an inwardly crimped concavity of said matrix occlusal edge.

22. A lock loop according to claim 18, wherein said concavity is formed to sandwich said matrix occlusal edge into an inwardly crimped concave pocket formation which when said matrix is tightened on a tooth, said plastic occlusal edge, and concavity stiffen from said tightening, sufficient to rigidly pocket the occlusal portion of the lock loop in said stiffened concaved crimped matrix film pocket against lateral pivoting and loosening of the lock loop and matrix, thereby retaining the locked matrix on the tooth until the lock-loop is severed for the purpose of removing the matrix when restoration of a tooth is completed.

23. A dental matrix band for engaging around a tooth, comprising: a plastic sheet member having a windable portion carrying a first end of said sheet member, a curved intermediate tooth engaging portion carrying a second end of said sheet member, said second end of said sheet member defining a receiving area, said tooth engaging portion being wrapped to form a matrix band with a part of said tooth engaging portion which is adjacent to said windable portion overlying said receiving area, said windable portion being wound to form a winding coil, and a lock loop engaged over said receiving area and said part of said tooth engaging portion, said lock loop permitting a sliding withdrawal of said tooth engaging portion with a winding of said winding coil by a dentist's matrix coil winding tool to tighten said band around a tooth by winding said coil against said lock loop which locks the matrix on the tooth, said matrix band having a laminate laminated to said receiving area with said laminate extending laterally beyond the band's lock-loop retaining portion in said area, so as to underlie said windable coil which is adjacent said lock-loop, with said extended laminate serving to thicken said area underlying said coil, so that said laminate can serve as a support to the area underlying said winding coil to thereby support and resist said coil's inwardly winding pressure on said area to thereby prevent said area from collapsing under said pressure of said inwardly winding coil, which windingly bears against said area, thus resisting the wrap-under forces of said winding coil, and resisting thereby said coil's inclination to wrap itself under said supported area and thereby avoiding said coil from becoming wrappingly entangled with said lock-loop which is adjacent said winding coil.

24. A matrix band according to claim 23 including an elongated laminate laminated to said receiving area and extending partly onto said tooth engaging portion for underlying said coil for supportively reinforcing said band against wrap-under force resulting from winding of said coil.

25. A dental matrix according to claim 23 wherein said laminate has an inclined edge which is inclined at an angle toward said gingival tooth contacting point of said lock loop.

26. A matrix band according to claim 23 including an elongated laminate laminated to said receiving area and extending partly onto said tooth engaging portion for underlying said coil for reinforcing said band against wrap-under forces resulting from winding of said coil

* * * * *